United States Patent
De Maeztu Martinez et al.

(10) Patent No.: US 7,122,810 B2
(45) Date of Patent: Oct. 17, 2006

(54) METHOD FOR MANUFACTURING ENDO-OSSEOUS IMPLANTS OR MEDICAL PROSTHESIS BY IONIC IMPLANTATION TECHNIQUE

(75) Inventors: Miguel Angel De Maeztu Martinez, San Francisco, 43 A 1ª Dcha., 20440 Tolosa (Guipuzcoa) (ES); José Iñaki Alava Marquinez, Guipuzcoa (ES); Alberto Garcia Luis, Guipuzcoa (ES); Iñigo Braceras Izaguirre, Guipuzcoa (ES); Jose Ignacio Oñate De La Presa, Guipuzcoa (ES)

(73) Assignees: Fundaction Inasmet (ES); Miguel Angel De Maeztu Martinez (ES)

( * ) Notice: Subject to any disclaimer, the term of this patent is extended or adjusted under 35 U.S.C. 154(b) by 253 days.

(21) Appl. No.: 10/474,660

(22) PCT Filed: Apr. 11, 2002

(86) PCT No.: PCT/ES02/00178

§ 371 (c)(1),
(2), (4) Date: Oct. 14, 2003

(87) PCT Pub. No.: WO02/083977

PCT Pub. Date: Oct. 24, 2002

(65) Prior Publication Data

US 2004/0106994 A1 Jun. 3, 2004

(30) Foreign Application Priority Data

Apr. 16, 2001 (ES) .......................................... 200100873

(51) Int. Cl.
*A61F 62/28* (2006.01)

(52) U.S. Cl. .................. 250/492.3; 433/173; 623/16.11
(58) Field of Classification Search .............. 250/492.3; 433/173; 623/16.11; 427/523, 530, 569
See application file for complete search history.

(56) References Cited

U.S. PATENT DOCUMENTS

| | | |
|---|---|---|
| 4,693,760 A | 9/1987 | Sioshansi |
| 5,133,757 A | 7/1992 | Sioshansi et al. |
| 6,033,582 A * | 3/2000 | Lee et al. ...................... 216/37 |
| 6,051,751 A | 4/2000 | Sioshansi et al. |
| 6,217,615 B1 * | 4/2001 | Sioshansi et al. ........ 623/18.11 |
| 6,368,676 B1 * | 4/2002 | Gaudreau et al. ........... 427/523 |

FOREIGN PATENT DOCUMENTS

| | | |
|---|---|---|
| ES | 2 045 487 | 1/1994 |
| GB | 2154450 A | 9/1985 |
| GB | 2 286 347 A | 8/1995 |
| WO | WO 91/16013 | 10/1991 |
| WO | WO 01/49339 A1 | 7/2001 |

\* cited by examiner

*Primary Examiner*—John R. Lee
*Assistant Examiner*—James J. Leybourne
(74) *Attorney, Agent, or Firm*—Michael Best & Friedrich LLP

(57) ABSTRACT

The method comprises the ion implantation of controlled quantities of elements such as CO, C or O in endo-osseous implants or prostheses manufactured in metals, metallic alloys or biocompatible compound materials. This surface treatment originates some modifications in the characteristics of the surface of the endo-osseous implants or prostheses which increases significantly their degree of osseointegration.

10 Claims, 5 Drawing Sheets

METHOD FOR MANUFACTURING ENDO-OSSEOUS IMPLANTS OR MEDICAL PROSTHESIS BY IONIC IMPLANTATION TECHNIQUE

This application claims the benefit of International Patent Application No. PCT/ES02/00178 filed 11 Apr. 2002, which claims priority of Spanish Patent Application No. P200100873 filed 16 Apr. 2001.

FIELD OF THE INVENTION

This invention is related, in general, with surface treatments of implants and medical prostheses to improve their osseointegration properties, in particular, it refers to a method for the production of endo-osseous implants or prostheses manufactured in a base material and treated superficially by means of ion implantation with enhanced osseointegration properties.

BACKGROUND OF THE INVENTION

The requirement for prosthetic treatments of long duration (implants or knee, hip, maxillofacial, cranial, etc. prostheses), is increasingly usual in daily clinical practice, and involves the use, in numerous cases, of metallic materials (subcutaneous or osseous implants) mainly in patients subjected to major traumatic surgery, maxillofacial surgery, osteoporotic and osteoproliferative patients. The employment of these systems of prosthetic substitution is accompanied by a not insignificant implant failure rate, which in some cases surpasses 30%, and at times makes recourse to this technique an impossibility.

The most frequent complications encountered, described in the medical literature, are the infectious type (infection of the implant, bacteremia, sepsis, and others less frequent, like gangrene, etc.), the inflammatory type (reaction to a foreign body, local inflammation, total rejection), those of tissue integration (gingivitis, sinovial metallosis, osteoresorption) and those arising from their handling and use (rupture of the bone, failure of the metal-tissue interface).

The biocompatible metals constitute the most important and diverse group of materials used in biomedical applications because they offer appropriate properties of biocompatibility and chemical inertia which make them suitable for contact with biological fluids and tissues. Also, they have the characteristic that they can be manufactured in a great variety of ways.

However, the evolution observed in recent years regarding the types of alloys employed has not reduced the number of complications as much as would have been expected and the experimental procedures used to improve their biocompatibility have been limited to more permeable designs or surface impregnations, more or less intense, with molecules having biological activity (antibiotics, antiseptics, antiaggregants, etc.).

The requirement remains to develop medical materials whose employment permits avoidance of the entirety or part of the aforementioned complications.

In that concerning the problem of osseointegration of the prostheses or implants, a method of approaching the problem could consist in applying a surface treatment thereon which confers upon them the appropriate characteristics.

This is the case of ion implantation, a treatment which does not modify the structural properties or the dimensional tolerances of the treated prostheses or implants (see FIG. 1) but which, however, can modify their surface properties by means of the introduction of a series of selected elements on the surface, modifying the properties thereof in the desired sense.

Use has been made of different techniques of ion implantation for many years in different fields of application with the object of modifying the surface properties of the components. It is used, for example, in electronics for modification of the electrical properties of semiconductors. It is also applied in the metal mechanics industry for the improvement of properties of resistance to abrasion and corrosion, in cases such as moulds and injection mouthpieces, machining and cutting tools, gauges, etc.

Ion implantation has also been used on biomaterials. This is the case, for example, of the implantation of germicidal elements in medical equipment described in U.S. Pat. No. 5,492,763, or the implantation in implants of cobalt-chromium alloys with the object of increasing surface hardness and reducing friction as described in European patent application EP 526 581. The problem of osseointegration has also been broached from the ion implantation technique in order to produce a surface coated with hydroxyapatite, a coating which has also been applied by other processes. Such is the case of the method for the production of surgical implantations coated with synthetic bone described in Spanish patent ES 2.006.658 which employs high energy streams of xenon to coat the implants with hydroxyapatite by the sputtering or cathodic spraying technique. German patent application DE 19830530 describes the production of titanium surfaces coated with calcium phosphate by ion implantation. In this last case, use is made of phosphorus and calcium implantation followed by a heat treatment.

Notwithstanding the existence of previous applications of ion implantation in implants and medical prostheses, the ion implantation methods employed provide implants and prostheses with insufficient osseointegration properties and/or with a risk of lixiviation of the ions to the physiologic medium in contact with the inadequate implants and prostheses, and/or with not completely satisfactory tribological properties.

SUMMARY OF THE INVENTION

The invention confronts the problem of providing endo-osseous implants and prostheses, superficially treated by ion implantation, with characteristics of enhanced osseointegration.

The solution provided by this invention comprises the development of a method for the production of said implants and medical prostheses designed to overcome the problems of osseointegration thereof in the osseous structures and is based in that the ion implantation of controlled quantities of certain elements and/or compounds in said implants or prostheses, under certain conditions, allows endo-osseous implants and/or medical prostheses to be obtained with an enhanced degree of osseointegration thereof, and/or with a reduced degree of lixiviation of ions to the physiological medium, and/or with enhanced tribological properties.

DETAILED DESCRIPTION OF THE INVENTION

Figure 1:
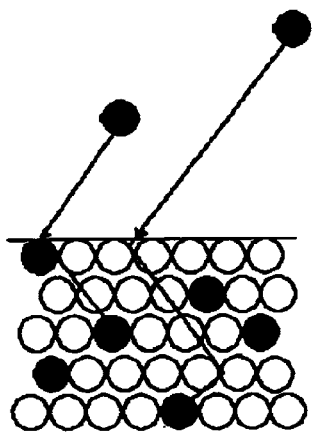
In FIG. 1 a simplified diagram of the ion implantation process can be seen. The ions are accelerated by application of high electromagnetic fields, and impact on the surface of the material, being inserted in the material. This process is carried out without originating any modification in the surface dimensions of the implanted material, but nevertheless its physico-chemical properties are modified.
Figure 2:
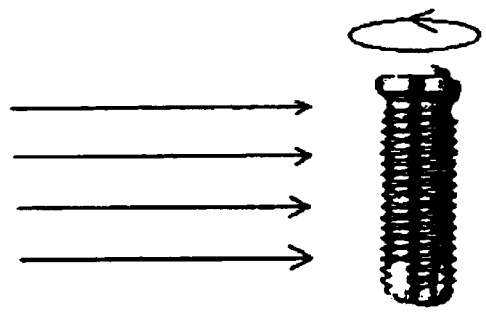
In FIG. 2 detail of an embodiment is shown in which the beam of ions impacts directly on a dental implant, at the same time as the latter is subjected to a rotational movement. The beam can impact the piece from different directions, so that it is assured that the whole surface of the implant is subjected to the ion implantation treatment.
Figure 3:
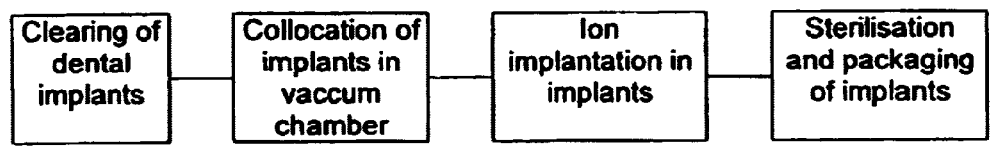
In FIG. 3 a simplified schematic of a typical process for manufacturing dental implants can be seen.

The invention provides a method for the production of endo-osseous implants or medical prostheses, hereinafter method of the invention, said endo-osseous implants or medical prostheses being manufactured from a base material, by means of a surface ion implantation treatment of, at least, an element selected among the elements C, O, H, Xe, Ar, He, Kr, Ne and/or a compound which comprises one or more of said elements, in which an ion beam energy is used of between 1 keV and 1 MeV, in which the process of ion implantation is carried out in a vacuum chamber with a vacuum better than $10^{-3}$ millibars and a dose is applied of, at least, $10^{15}$ ions/cm$^2$.

The term endo-osseous implants or medical prostheses, as it is employed in this description includes whatever endo-osseous implant or prostheses intended to be in contact with living tissues or cells, or with corporal or biological fluids.

As base material use can be made of any metal, metallic alloy, biocompatible material, and mixtures thereof, employed in the elaboration of endo-osseous implants and/or medical prostheses, such as those materials which satisfy the standard UNE-EN ISO 10993. In a particular embodiment, said base material is selected among titanium; alloys of titanium, aluminium and vanadium, for example, Ti-6Al-4V; alloys of chromium and cobalt (Cr—Co); alloys of cobalt, chromium and molybdenum (Co—Cr—Mo), stainless steel, for example, AISI 316 stainless steel, etc.

The method of the invention comprises the implantation of, at least, an ion of an element selected among the elements C, O, H, Xe, Ar, He, Kr, Ne and/or of an ion of a compound which comprises one or more of said elements, for example, CO, CO$_n$, CxHy, etc. (where n is an integer between 1 and 2, and x and y are integers between 1 and 100.)

The method of the invention is carried out, advantageously, in a treatment or vacuum chamber with a vacuum level of, at least, $10^{-3}$ millibars.

Ion implantation, according to the method of the invention, can be carried out, optionally, in presence of a residual atmosphere in said vacuum chamber. This residual atmosphere can consist both in the presence of oxygen and of residual organic compounds, for example, organic compounds produced by the evaporation of an organic compound during the process of ion implantation in the treatment chamber. The implanted ionic doses can vary within a wide range depending on the nature of the implanted ion, being, in general, greater than $10^{15}$ ions/cm$^2$ with the object of providing the endo-osseous implant or the medical prostheses with the necessary properties to achieve a significant enhancement of the osseointegration capacity.

The process of ion implantation according to the method of the invention can be carried out over a wide temperature range, for example, it can be carried out at a temperature between –120° C. and 800° C., preferably, between ambient temperature and 250° C. In a particular embodiment, with the object of favouring mechanisms for diffusion, precipitation or transformation of compounds, the process of ion implantation according to the method of the invention can be carried out at a temperature of between 250° C. and 800° C. In other applications, these same mechanisms for diffusion, precipitation or transformation can be achieved by means of heat treatment of the endo-osseous implants or prostheses, when the process of ion implantation has been completed, at a temperature of between 250° C. and 800° C.

The ion implantation treatment, according to the method of the invention, can be applied to endo-osseous implants or medical prostheses by means of techniques of line of sight ion implantation or beam ion implantation, plasma immersion ion implantation or plasma source ion implantation, or by means of whatever other equivalent technique.

As a result of the method of the invention endo-osseous implants or medical prostheses can be obtained, for example, dental implants, prostheses of hip, knee, etc., with an enhanced degree of osseointegration thereof, and/or with a reduced degree of lixiviation of ions to the physiological medium in contact with said implants and/or prostheses, and/or with enhanced tribological properties, for example, better resistance to abrasion, decreased friction, etc.

The endo-osseous implants and prostheses attainable by means of the method of the invention constitute an additional object of this invention. In a particular embodiment, said endo-osseous implants or prostheses have an enhanced degree of osseointegration, and/or a reduced degree of ionic lixiviation to the physiologic medium in contact with the implant or the prostheses, and/or enhanced tribological properties.

The following example of embodiment illustrates the invention and should not be taken restrictively with regard to the scope thereof.

EXAMPLE

Ion Implantation of CO$^+$ Ions in a Dental Implant

Figure 4:
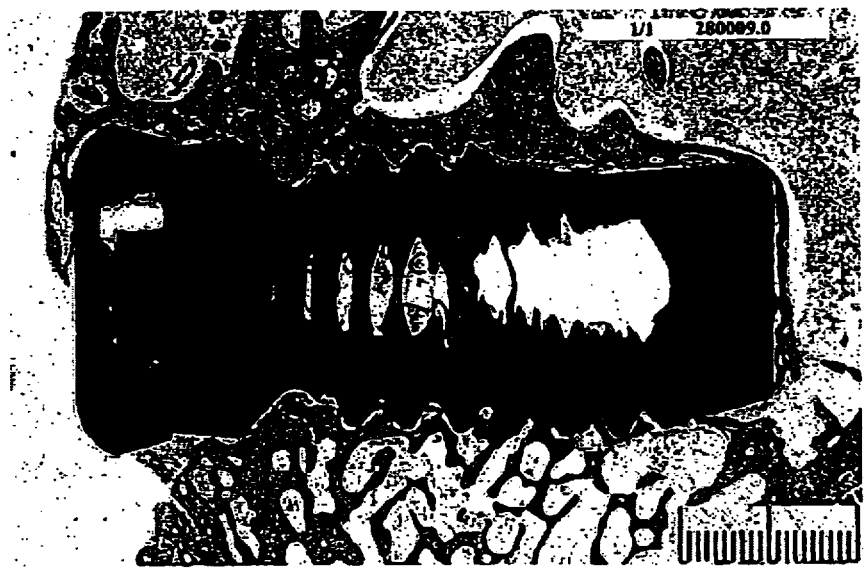
FIGS. 4 and 5 show the aspect of a cross-section of the implants largely surrounded by osseous matter. The samples were prepared have with Martins and Masson staining, respectively.
Figure 5:

This example illustrates the application of a surface ion implantation treatment of CO$^+$ ions in a dental implant manufactured in a titanium alloy Ti6Al4V. For it, 8 Spline Twist TiTM (Sulzer Calcitek Inc.) commercial dental implants were selected, 8 mm long by 3.75 mm diameter. They are smooth-surface machined screws manufactured in Ti6Al4V. For the subsequent tests, other 8 dental implants of the same batch were reserved without treatment. In FIGS. 4 and 5 the appearance of these screws can be seen in cross-section.

The dental implants were cleaned successively in an ultrasonic bath of acetone and ethanol for a minimum period of time of 5 minutes. Subsequently they were all introduced in the vacuum chamber. The vacuum level that was reached and maintained during the entire ion implantation process was at all times better than $5.10^{-7}$ millibars.

The ion implantation treatment was carried out in an Ion Implanter of the 1090 series by Danfysik AS, located in the facilities of Inasmet in Irun. The dental implants were implanted ionically with $CO^+$ ions, at an energy of 50 keV with a dose of $5.10^{17}$ ions/cm$^2$. This treatment was applied to the lateral cylindrical surface and the end surface of the thread of the dental implants. The temperature of the dental implants did not reach at any time values of more than 170° C.

In FIG. 1 a simplified schematic of a typical manufacturing process of dental implants can be observed.

According to estimates made with the "Profile Code" software package, the element implanted under these conditions is in regions of less than 0.1 µm in depth, atomic concentrations being reached of more than 25% for both elements in the areas of maximum concentration and normal incidence of the ion beam.

The treatment of dental implants by the ion implantation technique described above allows the implant failure rate to be reduced, due to an increase in the degree of osseointegration of the dental implants in the osseous mass. This has been demonstrated by means of osseous implantation tests.

Osseous Implantation Test

Screws of Ti6Al4V with $CO^+$ ion implantation have been tested by means of the "bone implantation test" according to standard UNE-EN 10993-6:1995.

The objective of this test was to evaluate the biological response of the osseous tissue to the implanted material. The method compares the biological response to implants in test samples with the biological response to implants in control samples.

Animals

Rabbits were used, mature male albinos (New Zealand White), animal model with osseous structures of sufficient mass to receive the dental implants, the mean weight of which was 4700 g, with a minimum of 4000 g and a maximum of 5200 g. They have been kept and cared for according to the ISO 10993-2:1992 standard and in compliance with the legal regulations of the Ministry of Agriculture, Fishing and Foodstuffs RD 223/1988, Order dated Oct. 13, 1989.

Samples 8 smooth-surface machined screws manufactured in Ti6Al4V, 8 mm long by 3.75 mm diameter, and implanted ionically with $CO^+$ according to the previously described procedure.

Control 8 smooth-surface machined screws manufactured in Ti6Al4V, 8 mm long by 3.75 mm diameter, similar to the samples were used as control samples.

Place of Implantation 4 screws per rabbit implanted in the tibial plateau.

Operating Procedure

A general anaesthesia was applied with tiacine hydrochlorate of 3.15 mg/500 g intramuscular (i.m.) (ROMPUN 2%®) and ketamine 18 mg/500 g i.m. (KETOLAR 50®), completed with local anaesthesia in the intervention area with lidocaine 1:100.000, 1 ml in each leg. After shaving and disinfection of the area, deferred cutaneous incision was carried out, with sterile technique, separation of the fascias and distal inserts of the internal straight and semi-tendinous muscles and of the proximal insert of the cranial tibial muscle and detachment of the periosteum of the front face of the proximal epiphysis of both tibias.

With micromotor and cooling with physiological serum, the osseous cortical mass was drilled at 1500 revolutions/minute, using a ball bit. Next, the implant osseous channel was deepened to 8 mm with bits with external cooling of 2 mm in diameter and internal of 3 mm and bit of 3.3 mm in diameter, with external irrigation, followed by diestock. The ionically implanted and control dental implants were placed in the channel by manual insertion employing a ratchet key. The wound was closed by planes with polyglactin suture 4/0 (Vycril®) and the skin with silk 3/0 (Arago®).

Antibiotic prevention was administered with benzylpenicillin benzathine $50\times10^3$ U/kg/week i.m. (BENZETACIL 1.200.000®). Locally, after shaving the paws at the level of the tibial plateaux, iodized povidone (Betadine®) was applied on the area. During the following days analgesic treatment was administered with acetil salicylate of lysine 10 mg/500 g, i.m. (INYESPRIN®). In the days following, the areas of the surgical wounds were cleaned and 0.12% chlorhexidine and antibiotic ointment (Furacin®) was applied locally.

The animals remained for three months housed individually in a controlled medium with light/darkness cycles (12 h), air conditioning (15 renovations/h) and at a temperature controlled between 18° C. and 22° C., complying with the legal regulations in this respect.

After sedation with diazepam 5 mg/kg i.m. (Valium®), the animals were sacrificed using a carbon monoxide chamber, the tibial plateaux containing the implants were extracted in block and introduced in 4% formol for later processing thereof.

The osseous blocks, containing the implants, were subjected to a technique of desiccation and dehydration in 60%, 80%, 96% and 100% acetones and alcohols, concluding in 100% xylol. Later separation, cutting and fine polishing were carried out according to the DONATH technique, for obtaining histological sections. To make microscopic study possible, the samples were subjected to staining. An example of the appearance of these samples can be seen in FIGS. 4 and 5.

Appraisal of Results

1. Histological Evaluation

The evaluation of the histological preparations was done by means of prior capture of images with a digital macrophotography system (Nikon). The images so obtained were analysed by means of an Omnimet image analyser, and processed with an image handling program Adobe Photoshop 5.0.

When defining the osseointegrated area the following criteria were adopted:

The area in contact with spongy or trabecular bone was not considered osseointegrated, only that with cortical bone.

The adjacent areas were considered osseointegrated which for contour similarity with the cortical bone could be assumed to have been displaced in the preparation process.

Those areas were considered osseointegrated which, in a computer amplification of the area (×200) showed small and fine layers of cortical osseous tissue adhered to the implant.

Considered as osseointegrated as a single area were those adjacent integrated areas, the separation distance of which was less than one quarter of the width of the thread of the implant.

Figure 6:
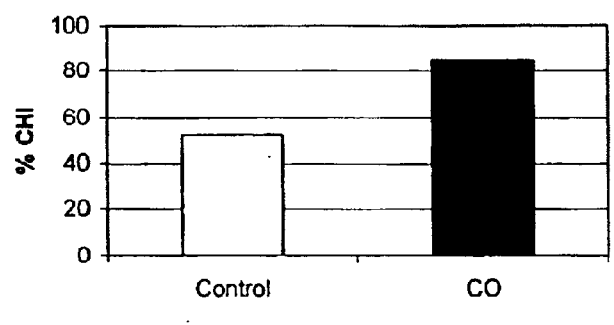
FIG. 6. is a chart indicating the bone implant contact percentage (CHI) of dental implants implanted in the epiphyseal area (distal), an untreated control implnat and a CO ion treated implant are represented.

The results showed statistically significant differences between the implants located on the tibia of the rabbit in the epiphyseal area (distal) or metaphyseal area (mesial), osseointegration being more difficult in the first case, as it concerns an area poorer in cortical bone. In this last case, a significantly greater bone-implant union was appreciated in the case of implants with ion implantation treatment, as can be observed in FIG. 6.

2. Study by Means of Electronic Microscopy

Figure 7:
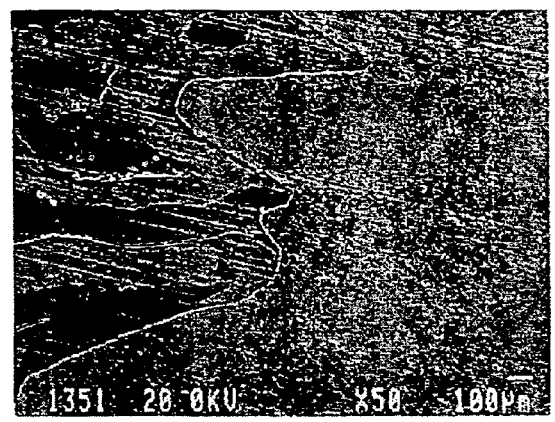
FIGS. 7 and 8 are photographs taken with a sweeping electronic microscope, in which the close contact can be observed of the osseous matter with the surface of the implant which has been subjected to ion implantation treatment.
Figure 8:
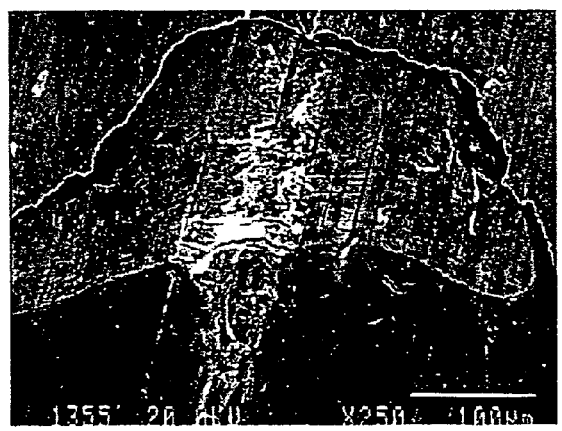
Figure 9:
FIGS. 9, 10, 11 and 12 are some photographs taken with a sweeping electronic microscope which show different details at different magnifications of the osseous structure after removal of the treated implant.
Figure 10:
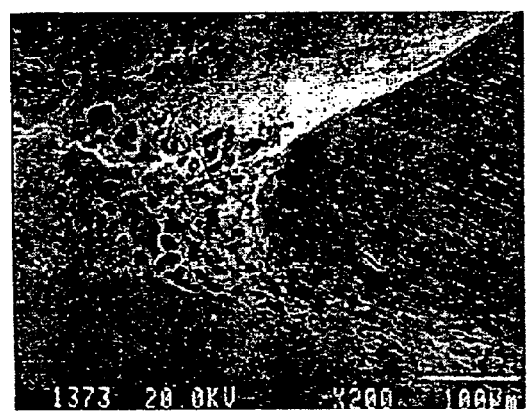
Figure 11:
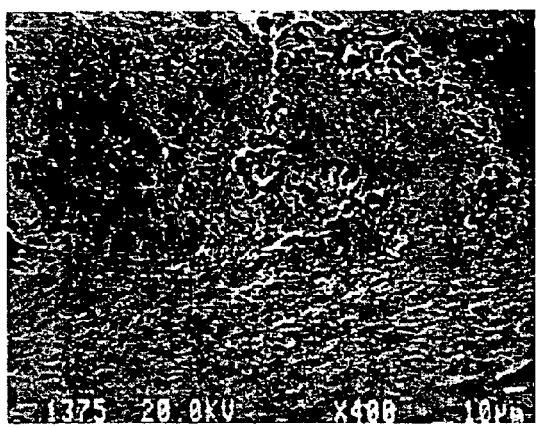
Figure 12:
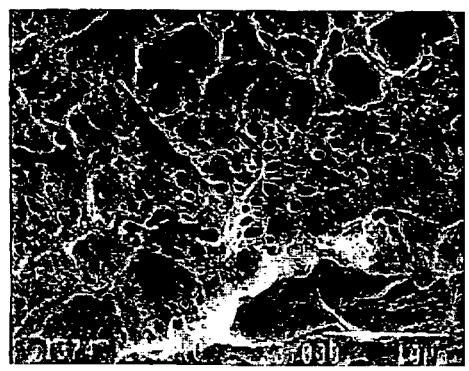

The type of union was analysed between the bone and the implant. In FIGS. 7 and 8 a close contact can be observed between bone and implant at different magnifications. The whiter images correspond to bone and the darker to soft tissue. This was checked by a composition analysis by electron microprobe (EDS) of both areas.

Also, in one of the samples the implant of the histological section was removed and the bone observed from the cavity of the implant. The images allow the osseous structure in contact with the implant to be seen clearly (see FIGS. 9, 10, 11 and 12).

3. Study by Means of XPS

Figure 13:
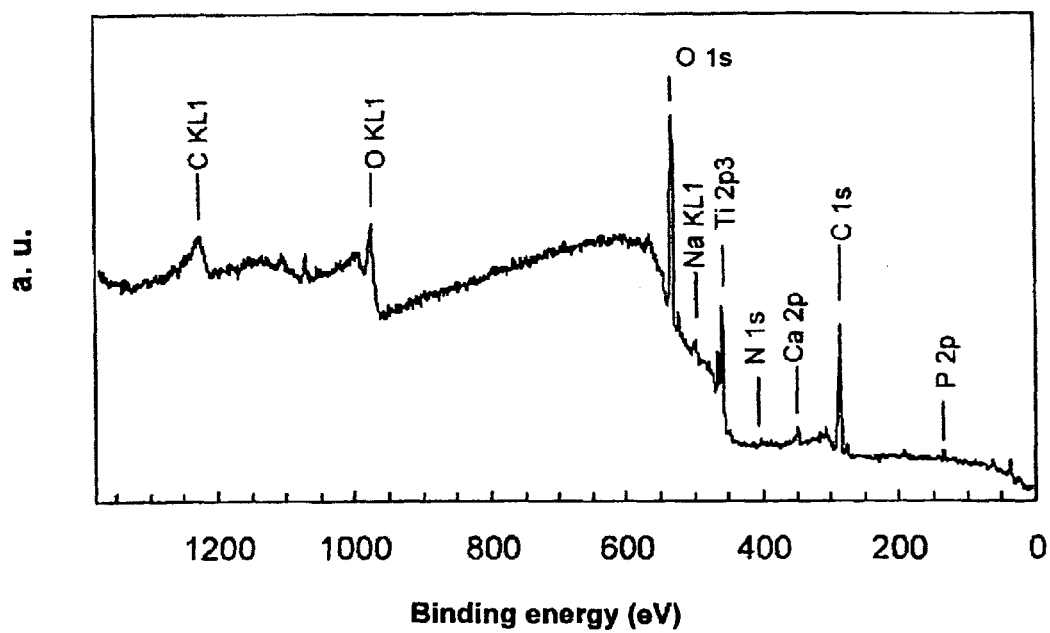
In FIG. 13 the XPS spectrum is shown, with the bonding energies of the elements present in the atomic layers of the bone-implant interface, of a sample subjected to the ion implantation treatment.

By means of this technique the composition of the elements present in the atomic layers of the bone-implant interface was analysed, and the type of linkage between the titanium and the osseous tissue to which it is joined (FIG. 13).

It was observed that maximum energy was at a binding energy corresponding to a Ti—O—C bond, where the carbon belonged to a complex organic molecule. Said Ti—O—C bond present in the interface of the surface of the implant corresponds to the protein-metallic oxide union formed during the period of permanency in the living animal.

CONCLUSION

Surface ion implantation treatment with $CO^+$, induces changes in physical structure and surface electrochemistry, increasing adhesion to the surrounding biological tissue.

The histomorphometric results obtained confirm the improvement in osseointegration, in terms of bone implant contact.

Additionally, ionic implantation improves tribological properties, increasing the resistance of the material treated to wear and abrasion, it increases resistance to corrosion and chemical attack, reducing the possibility of electrochemical reaction with the medium, therefore diminishing lixiviation of the material.

What is claimed:

1. A surface treatment method for the production of endo-osseous implants or medical prostheses, said endo-osseous implants or medical prostheses being manufactured from a base material, by means of a surface ion implantation treatment of CO and/or a compound which comprises CO, e.g., $C_aO_bH_c$ or $C_aO_bH_cN_d$ in which an ion beam energy is employed of between 1 keV and 1 MeV, in which the process of ion implantation is carried out in a treatment chamber with a vacuum better than $10^{-3}$ millibars and a dose is applied of, at least, $10^{15}$ ions/cm$^2$.

2. Method according to claim 1, in which said base material is selected among a metal, a metallic alloy, a biocompatible ceramic, and mixtures thereof, i.e. composites employed in the elaboration of endo-osseous implants and/or medical prostheses.

3. Method according to claim 2, in which the process of ion implantation takes place in presence of a residual atmosphere of oxygen or of organic compounds in the treatment chamber.

4. Method according to claim 3, in which an organic compound is evaporated during the process of ion implantation in the treatment chamber.

5. Method according to claim 4, in which the process of ion implantation is applied on said endo-osseous implants or medical prostheses by means of techniques of line of sight ion implantation or beam ion implantation, plasma immersion ion implantation or plasma source ion implantation, or ion bombardment techniques.

6. Method according to claim 5, in which the process of ion implantation is carried out at a temperature between −120° C. and 800° C.

7. A surface treatment method for the production of endo-osseous implants or medical prostheses, said endo-osseous implants or medical prostheses being manufactured from a base material, by means of a surface ion implantation treatment of CO and/or a compound which comprises CO, e.g., $C_aO_bH_c$ or $C_aO_bH_cH_d$ in which an ion beam energy is employed of between 1 keV and 1 MeV, in which the process of ion implantation is carried out in a treatment chamber with a vacuum better than $10^{-3}$ millibars and a dose is applied of, at least, $10^{15}$ ions/cm$^2$. in which the endo-osseous implants or the prostheses undergo a thermal treatment at a temperature of between approximately 250° C. and 800° C. after the process of ion implantation.

8. An endo-osseous implant or medical prostheses, where at least the surfaces to be in contact with bone are treated, by the method of claim 1.

9. Endo-osseous implant or medical prostheses according to claim 8, in which said implant or prostheses has an enhanced degree of osseointegration.

10. Method according to claim 9 for dental implants wherein said osseointegration is typically increased from around 50% to around 80% in poor bone areas, and/or a reduced degree of ionic lixiviation to the physiologic medium in contact with the implant or the prostheses.

* * * * *